United States Patent
Suzuki et al.

(10) Patent No.: US 12,044,670 B2
(45) Date of Patent: Jul. 23, 2024

(54) CASTING METHOD

(71) Applicants: SINTOKOGIO, LTD., Nagoya (JP); Fujiwa Denki Co., Ltd., Aichi (JP)

(72) Inventors: Umihiko Suzuki, Nagoya (JP); Tadashi Nishida, Aichi (JP); Toshiyuki Hyodo, Aichi (JP); Masanori Hoshino, Aichi (JP)

(73) Assignees: SINTOKOGIO, LTD., Nagoya (JP); Fujiwa Denki Co., Ltd., Aichi (JP)

( * ) Notice: Subject to any disclaimer, the term of this patent is extended or adjusted under 35 U.S.C. 154(b) by 0 days.

(21) Appl. No.: 17/893,448

(22) Filed: Aug. 23, 2022

(65) Prior Publication Data
US 2023/0067654 A1 Mar. 2, 2023

(30) Foreign Application Priority Data
Aug. 27, 2021 (JP) .................... 2021-139188

(51) Int. Cl.
*B22D 27/04* (2006.01)
*G01N 21/29* (2006.01)
*G01N 33/205* (2019.01)

(52) U.S. Cl.
CPC .......... *G01N 33/205* (2019.01); *B22D 27/04* (2013.01); *G01N 21/29* (2013.01)

(58) Field of Classification Search
CPC ....... B22D 27/04; G01N 33/205; G01N 21/29
See application file for complete search history.

(56) References Cited

U.S. PATENT DOCUMENTS 3,496,766 A * 2/1970 David .................. G01N 3/00
73/104

FOREIGN PATENT DOCUMENTS

WO WO-2017/085765 A1 5/2017

* cited by examiner

*Primary Examiner* — Kevin P Kerns
*Assistant Examiner* — Steven S Ha
(74) *Attorney, Agent, or Firm* — Faegre Drinker Biddle & Reath LLP

(57) ABSTRACT

A casting method includes pouring a molten metal in a ladle into a mold, analyzing at least one of a composition and a physical property of a test piece generated based on the molten metal sampled from inside the ladle, and performing appearance inspection of a casting product taken out from the mold, wherein in the performing appearance inspection, the at least one of the composition and the physical property of the test piece obtained in the analyzing is displayed on a display.

4 Claims, 2 Drawing Sheets

CASTING METHOD

CROSS-REFERENCE TO RELATED APPLICATION

This application is based on Japanese Patent Application No. 2021-139188 filed with Japan Patent Office on Aug. 27, 2021, the entire contents of which are hereby incorporated by reference.

TECHNICAL FIELD

The present disclosure relates to a casting method.

BACKGROUND

International Publication No. WO 2017/085765 discloses a casting facility. In this casting facility, a ladle receives a molten metal at a melting furnace and is conveyed to a pouring machine. Furthermore, a plurality of molds is molded by a molding machine and conveyed to the pouring machine on a mold-by-mold basis. At the pouring machine, the molten metal in the ladle is poured into the conveyed mold. The mold after the pouring is cooled with a long time being spent, and the molten metal solidifies before reaching a shake-out device, affording a casting product. The shake-out device takes the mold apart to take out the casting product. The casting product is, after its postprocessing, shipped as a product.

SUMMARY

Now, before casting products are shipped as products, the appearance and the like of the casting products are inspected. The inspection is performed, for example, by working personnel. The working personnel specify which product a casting product sequentially conveyed to an inspection site is, and determine whether or not the appearance of the casting product satisfies the standards as the product. Since it is general to manufacture, in the casting facility, a plurality of kinds of products, there is a concern that load on the working personnel in the inspection site before shipping increases. The present disclosure provides a casting method capable of efficiently performing inspection before shipping.

There is provided a casting method according to an aspect of the present disclosure, comprising: a pouring step of pouring a molten metal in a ladle into a mold; an analyzing step of analyzing at least one of a composition and a physical property of a test piece generated based on the molten metal sampled from inside the ladle; and an inspecting step of performing appearance inspection of a casting product taken out from the mold, wherein in the inspecting step, the at least one of the composition and the physical property of the test piece obtained in the analyzing step is displayed on a display.

In this casting method, in the inspecting step, the at least one of the composition and the physical property of the test piece obtained in the analyzing step is displayed on the display. Therefore, working personnel in the inspecting step can recognize the at least one of the composition and the physical property of the casting product to be inspected via the display. By the working personnel recognizing the at least one of the composition and the physical property of the casting product, work operation to specify a product corresponding to the casting product to be inspected becomes easy and accurate, and consistency of the composition and the physical property of the casting product with the appearance thereof can be observed. Therefore, this casting method can efficiently perform inspection before shipping.

In an embodiment, the casting method may comprise a sampling step of sampling the molten metal in the ladle used in the pouring step and generating the test piece, and in the analyzing step, the at least one of the composition and the physical property of the test piece generated in the sampling step may be analyzed. Since with such a configuration, the molten metal in the pouring step is sampled, a difference between the analysis result and the composition and the physical property of the casting product to be inspected can be reduced.

In an embodiment, the casting method may comprise: a cooling step of cooling the mold, the molten metal having been poured into the mold in the pouring step; and a shake-out step of taking out the casting product from the mold cooled in the cooling step, and in the inspecting step, the appearance inspection of the casting product taken out in the shake-out step may be performed.

In an embodiment, in the inspecting step, timing of the appearance inspection of the casting product and timing of displaying the at least one of the composition and the physical property of the test piece on the display may be synchronized. With such a configuration, the casting method can easily cause working personnel to understand correspondence between the casting product to be inspected and the analysis result of the relevant casting product.

According to various aspects and embodiments of the present disclosure, inspection before shipping can be efficiently performed.

DETAILED DESCRIPTION

Hereafter, an exemplary embodiment of the present disclosure will be described with reference to the drawings. Notably, in the following description, the same or corresponding elements are given the same signs and their duplicate description is not repeated.

Figure 1:
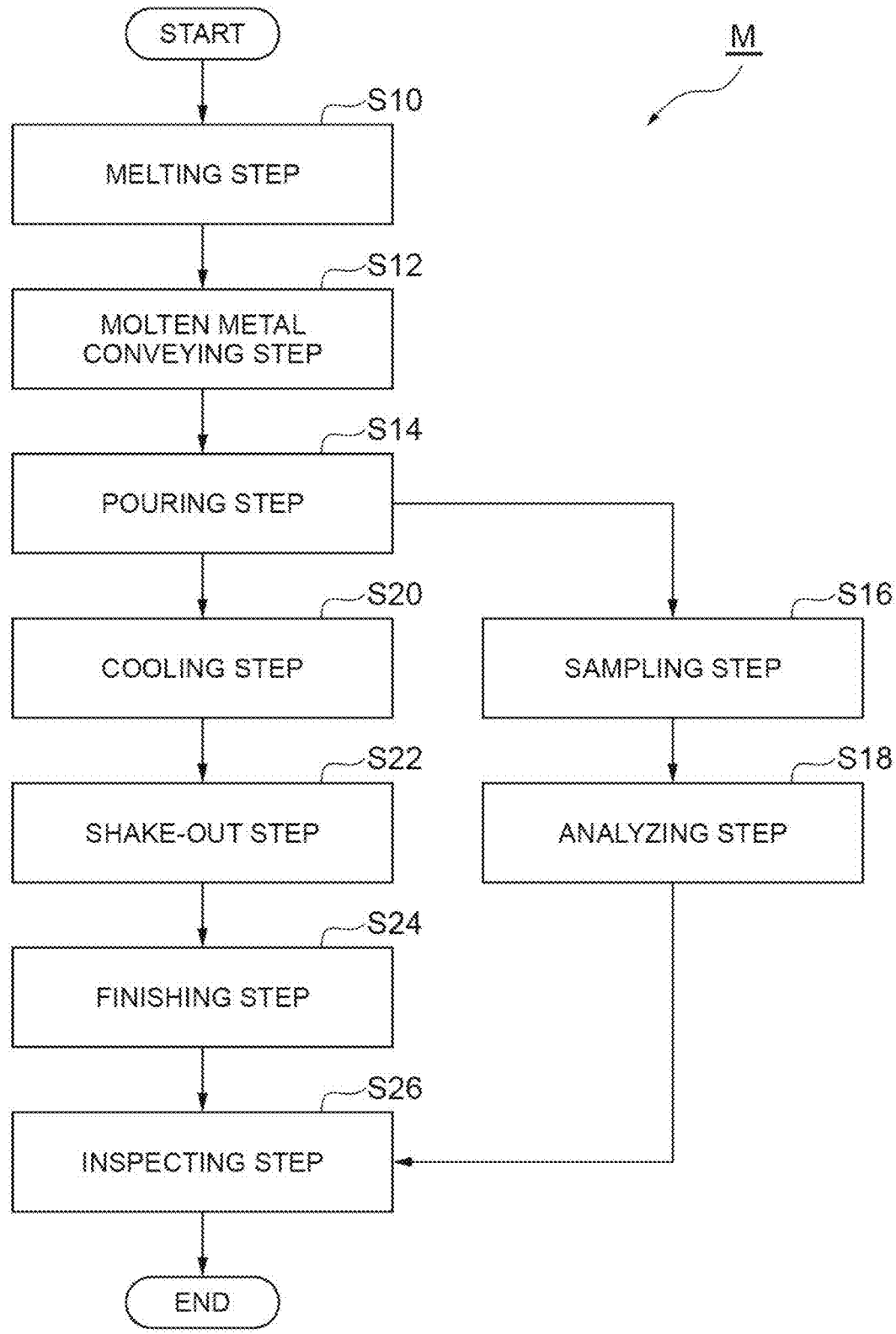
FIG. 1 is a flowchart of a casting method according to an exemplary embodiment.
Figure 2:
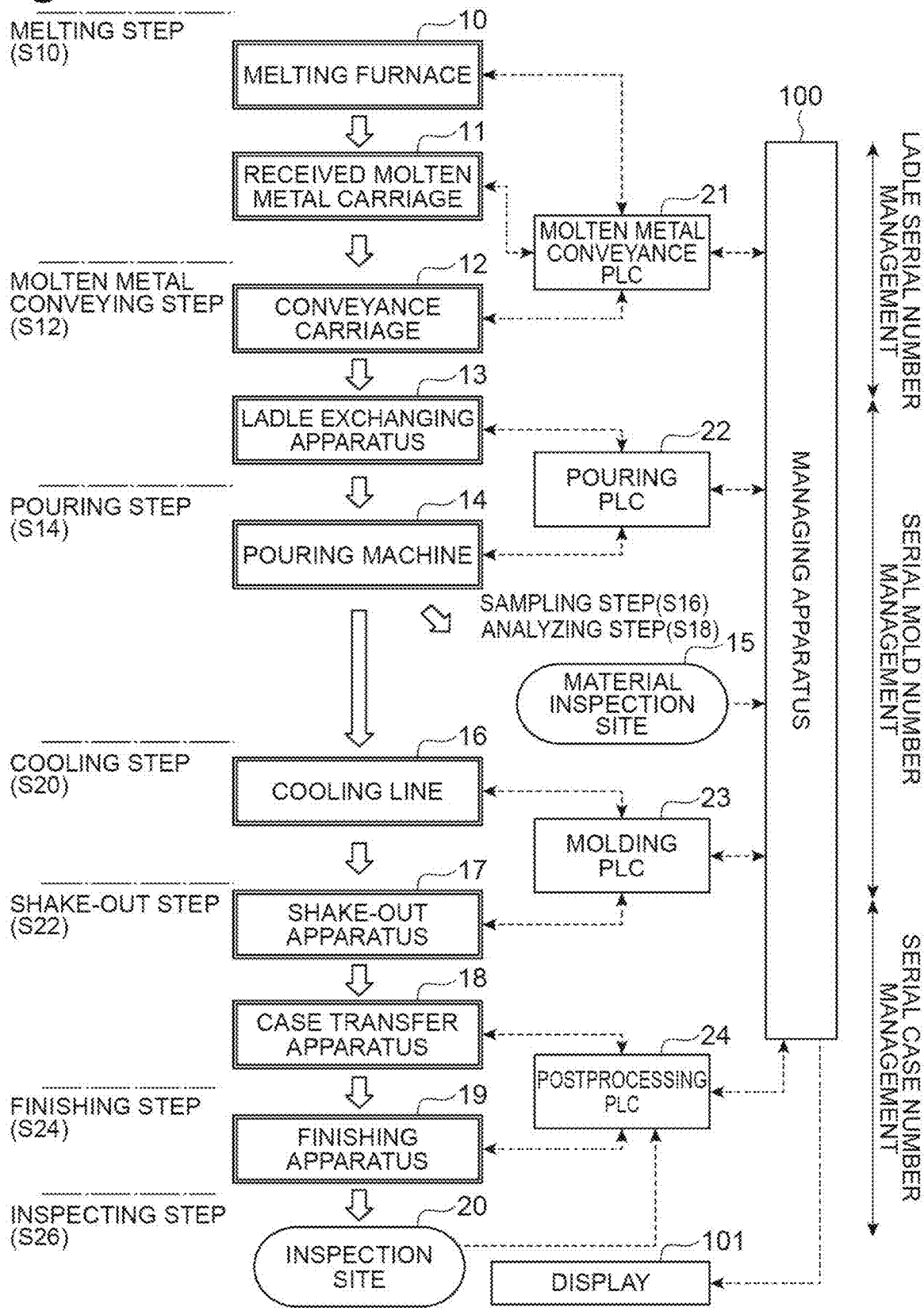
FIG. 2 is a diagram for explaining a casting facility in individual steps of a manufacturing method in FIG. 1.

FIG. 1 is a flowchart of a casting method according to an exemplary embodiment. A casting method M shown in FIG. 1 is implemented in a casting facility manufacturing casting products. As shown in FIG. 1, the casting method M includes a melting step (step S10), a melting/conveying step (step S12), a pouring step (step S14), a sampling step (step S16), an analyzing step (step S18), a cooling step (step S20), a shake-out step (step S22), a finishing step (step S24), and an inspecting step (step S26). Hereafter, the individual steps will be described with reference to FIG. 2. FIG. 2 is a diagram for describing the casting facility in the individual steps in a manufacturing method in FIG. 1.

[Melting Step (Step S10)]

As shown in FIG. 1 and FIG. 2, first, the melting step is performed. In the melting step, a melting furnace 10 melts a melting material with heat to obtain a raw molten metal. A molten metal produced by the melting furnace 10 is poured into a processing ladle. The processing ladle is conveyed with a received molten metal carriage 11. The processing ladle is conveyed to an emptying and exchanging position, and is emptied and exchanged for a ladle suitable for pouring (pouring ladle). The emptying and exchanging means transferring a molten metal to another ladle. The pouring ladle is conveyed with a conveying carriage 12. Operations of the melting furnace 10, the received molten metal carriage 11 and the conveying carriage 12 are controlled by a molten metal conveyance PLC (Programmable Logic Controller) 21.

Before pouring, for example, at the time of inputting a material for adjusting components of the molten metal or at the similar event, processing ladles are beforehand given ladle serial numbers. In timing of pouring to the processing ladle from the melting furnace 10, the molten metal conveyance PLC 21 associates information regarding the poured molten metal (molten metal information) and its ladle serial number with each other. To places where ladles can be moved, pieces of address information for specifying the places are beforehand assigned. The molten metal conveyance PLC 21 holds relationship between the ladle serial numbers and the pieces of address information. For example, when the ladle given the ladle serial number "1" is positioned at the place which the address information "2" indicates, the molten metal conveyance PLC 21 associates the ladle serial number "1" and the address information "2" with each other. The molten metal conveyance PLC 21 updates the aforementioned relationship every time when the ladle moves. For example, when the ladle given the ladle serial number "1" has moved from the position which the address information "2" indicates to the position which the address information "3" indicates, the molten metal conveyance PLC 21 associates the ladle serial number "1" and the address information "3" with each other. As above, by shifting the ladle serial number on data to meet the movement of the ladle, the molten metal conveyance PLC 21 can grasp the ladle positioned at an arbitrary place and refer to the molten metal information associated with the ladle serial number of the relevant ladle. Notably, when the molten metal in the processing ladle is transferred to a pouring ladle, the molten metal conveyance PLC 21 hands over the ladle serial number of the processing ladle to the pouring ladle and shifts the ladle serial number to meet the movement of the pouring ladle.

The molten metal conveyance PLC 21 transmits the ladle serial numbers and the pieces of molten metal information corresponding to the ladle serial numbers to a managing apparatus 100. The managing apparatus 100 is composed as an ordinary computer system including a PLC or a computer integrating the casting facility, physically, a CPU (Central Processing Unit), main storage devices such as a RAM (Random Access Memory) and a ROM (Read Only Memory), input devices such as a touch panel and a keyboard, an output device such as a display, an auxiliary storage device such as a hard disk drive, and the like.

[Molten Metal Conveying Step (Step S12)]

When the melting step completes, the molten metal conveying step is performed. In the molten metal conveying step, the conveying carriage 12 conveys the pouring ladle. The pouring ladle is conveyed by the conveying carriage 12. As well as at the aforementioned emptying and exchanging position, the conveying carriage 12 can stop also at a ladle exchange position where it conveys the pouring ladle to the pouring machine 14. Operation of the conveying carriage 12 is controlled by the aforementioned molten metal conveyance PLC 21.

At the ladle exchange position, a pouring ladle containing the molten metal (filled ladle) is handed over from the conveying carriage 12 to a ladle exchanging apparatus 13. With the ladle exchanging apparatus 13, exchange of the filled ladle and a pouring ladle having emptied through pouring (empty ladle) is implemented. Operation of the ladle exchanging apparatus 13 is controlled by a pouring PLC 22.

[Pouring Step (Step S14)]

When the molten metal conveying step completes, the pouring step is performed. In the pouring step, the pouring machine 14 pours the molten metal in the pouring ladle into a mold. In the pouring step, the molten metal is poured into a plurality of molds from one pouring ladle. To the pouring machine 14, a plurality of molds molded by a molding machine (not shown) are conveyed, with those caused to queue up, on a mold-by-mold basis. The pouring machine 14 pours the molten metal in the pouring ladle into the mold having been conveyed. Operation of the pouring machine 14 is controlled by the pouring PLC 22.

The pouring PLC 22 can acquire the ladle serial number and the molten metal information corresponding to the ladle serial number via the managing apparatus 100. Therefore, the pouring PLC 22 can acquire the molten metal information of the molten metal to be poured on the basis of the ladle serial number given to the pouring ladle to be used in pouring. Before pouring, for example, at the time of the manufacturing with the molding machine or at the similar event, molds are beforehand given serial mold numbers. In timing of pouring, the pouring PLC 22 associates the molten metal information and a serial mold number with each other. To places where molds can be moved, pieces of address information for specifying the places are beforehand assigned. The pouring PLC 22 holds relationship between the serial mold numbers and the pieces of address information. For example, when the mold given the serial mold number "1" is positioned at the place which the address information "2" indicates, the pouring PLC 22 associates the serial mold number "1" and the address information "2" with each other. The pouring PLC 22 updates the aforementioned relationship every time when the mold moves. For example, when the mold given the serial mold number "1" has moved from the position which the address information "2" indicates to the position which the address information "3" indicates, the pouring PLC 22 associates the serial mold number "1" and the address information "3" with each other. As above, by shifting the serial mold number on data to meet the movement of the mold, the pouring PLC 22 can grasp the mold positioned at an arbitrary place and refer to the molten metal information associated with the serial mold number of the relevant mold. The pouring PLC 22 transmits the serial mold numbers and the pieces of molten metal information corresponding to the serial mold numbers to the managing apparatus 100.

[Sampling Step (Step S16)]

The sampling step is performed before or after the pouring step or during the pouring step. In the sampling step, under the control by the pouring PLC 22, the pouring machine 14 samples the molten metal in the pouring ladle used in the pouring step and generates a test piece (TP). The pouring PLC 22 associates a test piece number and the ladle serial number with each other.

[Analyzing Step (Step S18)]

After the sampling step, the analyzing step is performed at a material inspection site 15. In the analyzing step, working personnel analyze at least one of the composition and the physical property of the test piece. The analysis result is transmitted, together with the test piece number and the ladle serial number, to the managing apparatus 100. The managing apparatus 100 stores the molten metal information corresponding to the ladle serial number and the analysis result, associating them with each other.

[Cooling Step (Step S20)]

The cooling step is performed after the pouring step. The cooling step can be performed in parallel with the sampling step and the analyzing step. In the cooling step, the cooling line 16 is conveying the molds with a long time being spent to cool the molten metals in the molds. Thereby, casting products are formed in the molds. Operation of the cooling line 16 is controlled by a molding PLC 23.

[Shake-Out Step (Step S22)]

The shake-out step is performed after the cooling step. In the shake-out step, a shake-out apparatus 17 takes the mold apart on a frame-by-frame basis to take out the casting product. Operation of the shake-out apparatus 17 is controlled by the molding PLC 23. The casting products thus taken out are placed in cases for every plurality of articles, are conveyed by a case transfer apparatus 18 on a case-after-case basis, and are transferred to a finishing apparatus 19. The case transfer apparatus 18 is controlled by a post-processing PLC 24.

The postprocessing PLC 24 can acquire the serial mold number and the molten metal information corresponding to the serial mold number via the managing apparatus 100. Therefore, the postprocessing PLC 24 can acquire the molten metal information corresponding to the mold having been taken apart in the shake-out step on the basis of the serial mold number. In timing of containing casting products in a case, the postprocessing PLC 24 associates the molten metal information and a serial case number with each other. To places where cases can be moved, pieces of address information for specifying the places are beforehand assigned. The postprocessing PLC 24 holds relationship between the serial case numbers and the pieces of address information. For example, when the case given the serial case number "1" is positioned at the place which the address information "2" indicates, the postprocessing PLC 24 associates the serial case number "1" and the address information "2" with each other. The postprocessing PLC 24 updates the aforementioned relationship every time when the case moves. For example, when the case given the serial case number "1" has moved from the position which the address information "2" indicates to the position which the address information "3" indicates, the postprocessing PLC 24 associates the serial case number "1" and the address information "3" with each other. As above, by shifting the serial case number on data to meet the movement of the case, the postprocessing PLC 24 can grasp the case positioned at an arbitrary place and refer to the molten metal information associated with the serial case number of the relevant case. The postprocessing PLC 24 transmits the serial case numbers and the pieces of molten metal information corresponding to the serial case numbers to the managing apparatus 100.

[Finishing Step (Step S24)]

The finishing step is performed after the shake-out step. In the finishing step, sand adhering to the casting product is removed with a blasting apparatus or the like, and the surface of the casting product is polished with a polishing apparatus or the like. Operations of these apparatuses are controlled by the postprocessing PLC 24.

[Inspecting Step (Step S26)]

The inspecting step is performed at an inspection site 20 after the finishing step and the analyzing step. In the inspecting step, working personnel perform appearance inspection of the casting products. The appearance inspection is a shape check, a sand removal check, a color check, a dimension check and the like under visual observation. In the inspection site 20, a display 101 connected to the managing apparatus 100 is arranged. During the inspecting step, the display 101 in the inspection site 20 displays the analysis result of the test piece on the basis of display control by the managing apparatus 100. The managing apparatus 100 specifies the molten metal information on the basis of the serial case number of the case having been transferred to the inspection site 20, specifies the analysis result associated with the molten metal information, and causes the display 101 to display the analysis result. Thereby, the working personnel in the inspection site 20 can recognize the at least one of the composition and the physical property of the test piece obtained in the analyzing step. The product number issued by the molding machine is also transferred to the managing apparatus 100 along with the test piece number and the like through the serial mold number management and the serial case number management.

In the inspecting step, the managing apparatus 100 can synchronize timing of the appearance inspection of the casting products and timing of displaying the analysis result on the display 101. The timing of the appearance inspection of the casting products may be manipulation timing of a working operation start button by the working personnel, may be timing when a sensor senses that the case is conveyed to the inspection site 20, or may be timing when a sensor senses the working personnel having been located at a working space in the inspection site 20. In response to acquiring the timing of the appearance inspection of the casting products, the managing apparatus 100 causes the display 101 to display the analysis result. Thereby, the timing of the appearance inspection of the casting products and the timing of displaying the analysis result on the display 101 are synchronized.

(Summary of Embodiment)

With the casting method M, in the inspecting step (step S26), at least one of the composition and the physical property of the test piece obtained in the analyzing step (step S18) is displayed on the display 101. Therefore, working personnel in the inspecting step can recognize at least one of the composition and the physical property of the casting product to be inspected via the display 101. By the working personnel recognizing the at least one of the composition and the physical property of the casting product, work operation to specify the product corresponding to the casting product to be inspected becomes easy and accurate, and consistency of the composition and the physical property of the casting product with the appearance thereof can be observed. Further, the managing apparatus 100 can further display a drawing or a photograph of the cast product on the display 101 based on the product number of the casting product, thereby improving work efficiency. Therefore, this casting method can efficiently perform inspection before shipping.

Moreover, since the molten metal in the pouring step (step S14) is sampled, a difference between the analysis result and the composition and the physical property of the casting product to be inspected can be reduced.

Furthermore, since in the inspecting step (step S26), the timing of the appearance inspection of the casting product and the timing of displaying the at least one of the composition and the physical property of the test piece on the display 101 are synchronized, the casting method M can easily cause the working personnel to understand correspondence between the casting product to be inspected and the analysis result of the relevant casting product.

While an exemplary embodiment has been described as above, various omissions, substitutions and alterations may occur without limitation to the aforementioned exemplary embodiment. For example, when there are a small number of ladles to be used, ladle serial numbers do not have to be used. Moreover, while in the exemplary embodiment, there has been exemplarily presented a configuration in which the PLCs communicate with one another via the managing apparatus 100, the PLCs may communicate directly.

REFERENCE SIGNS LIST

S14 . . . Pouring step, S16 . . . Sampling step, S18 . . . Analyzing step, S20 . . . Cooling step, S22 . . . Shake-out step, S26 . . . Inspecting step, 101 . . . Display.

What is claimed is:

1. A casting method comprising:
   pouring a molten metal in a ladle into a plurality of molds, wherein a serial mold number of each mold is associated with molten metal information corresponding to the molten metal information associated with the ladle
   analyzing at least one of a composition and a physical property of a test piece and acquiring as analysis results, the test piece generated based on the molten metal sampled from inside the ladle using the pouring, wherein the molten metal information is associated with the analysis results based on the molten metal information associated with the ladle;
   taking out a plurality of casting products from the plurality of molds, the plurality of casting products housed in cases, wherein the molten metal information is associated with a serial case number based on the serial mold number of each mold; and
   performing an appearance inspection of the plurality of casting products within each case transported to an inspection site where a display is located, at the inspection station, wherein
   the performing includes:
      acquiring the molten metal information corresponding to the plurality of casting products within each case based on the serial case number;
      determining the analysis results based on the molten metal information acquired; and
      displaying the determined analysis results on the display during the appearance inspection.

2. The casting method according to claim 1, further comprising:
   cooling the mold, the molten metal having been poured into the mold in the pouring.

3. The casting method according to claim 2, wherein in the performing appearance inspection, timing of the appearance inspection of the casting product and timing of displaying the at least one of the composition and the physical property of the test piece on the display are synchronized.

4. The casting method according to claim 1, wherein in the performing appearance inspection, timing of the appearance inspection of the casting product and timing of displaying the at least one of the composition and the physical property of the test piece on the display are synchronized.

* * * * *